(12) United States Patent
Ng et al.

(10) Patent No.: US 8,153,559 B2
(45) Date of Patent: Apr. 10, 2012

(54) CERTAIN PLANT GROWTH REGULATORS (PGRS) AS SAFENER TO GLYPHOSATE FOR APPLICATION TO GLYPHOSATE-TOLERANT CROPS

(75) Inventors: Denny Ng, Pomona, CA (US); Der-I Wang, Pomona, CA (US)

(73) Assignee: CP Bio, Inc., Chino, CA (US)

( * ) Notice: Subject to any disclaimer, the term of this patent is extended or adjusted under 35 U.S.C. 154(b) by 1349 days.

(21) Appl. No.: 11/538,562

(22) Filed: Oct. 4, 2006

(65) Prior Publication Data

US 2007/0105718 A1     May 10, 2007

Related U.S. Application Data

(63) Continuation-in-part of application No. 10/785,906, filed on Feb. 23, 2004, now abandoned.

(51) Int. Cl.
*A01N 57/18* (2006.01)
(52) U.S. Cl. .................................................. 504/206
(58) Field of Classification Search ..................... None
See application file for complete search history.

(56) References Cited

U.S. PATENT DOCUMENTS 5,525,576 A * 6/1996 Medina-Vega et al. ....... 504/358

\* cited by examiner

*Primary Examiner* — Alton Pryor
(74) *Attorney, Agent, or Firm* — Jen-Feng Lee, Esq.

(57) ABSTRACT

When the Glyphosate-tolerant crops, known as Round-Up Ready crops, are sprayed with Glyphosate in the field, the crops may exhibit some extent of phototoxicity, although the weeds are killed, as intended. Use of safener additive in present invention as plant growth regulator (PGR), along with Glyphosate, will result in reduced phototoxicity to the crops and thus better crops growth, while the herbicidal activities of Glyphosate are not affected.

3 Claims, No Drawings

CERTAIN PLANT GROWTH REGULATORS (PGRS) AS SAFENER TO GLYPHOSATE FOR APPLICATION TO GLYPHOSATE-TOLERANT CROPS

RELATED PRIOR APPLICATION

This application is a Continuation-In-Part (CIP) application, under 37 CFR 1.53(b), of a prior parent application Ser. No. 10/785,906, by the same inventors, to supplement the disclosure re the matter related to "Glyphosate solution". Present CIP application claims priority of the filing date of Feb. 23, 2004 now abandoned from the content already disclosed in the prior application, per the requirements of 35 U.S.C. §120 and 37 C.F.R. 1.78.

FIELD AND BACKGROUND OF THE INVENTION

Glyphosate, a chemical compound developed in the 1980s, has been used as an active ingredient of agricultural herbicides, especially in controlling major annual and perennial grasses and broad-leafed weeds. When applied to plants, Glyphosate inhibits the plant's EPSPS (5-enolypryuvylshikimate-3-phosphate synthase) enzyme.

The chemical composition and formula of Glyphosate is $C_6H_9Na_3N_2O_{10}P_2$. It's molecular weight is 422.09. The production of Glyphosate and its mechanism of inhibiting plant growth need not be discussed or disclosed and are not part of the claimed invention in present application.

Some crops, such as cotton, corns, soybeans and other "Glyphosate-tolerant" GMO crops, contain artificially modified EPSPS genes that make the crops tolerant to Glyphosate, at least as claimed by providers of such genetically modified crops. The term "Round-Up Ready" is widely used to describe these genetically modified crops that are claimed to be tolerant to Glyphosate, since the active ingredient in the Round-Up herbicide is Glyphosate.

Field tests on use of Glyphosate, however, showed substantial adverse effect to the growth of Round-Up Ready crops. This adverse effect is referred to as the Glyphosate's phytotoxicity in present application.

Present invention discloses the use of three PGR safener additives that can be mixed into Glyphosate solution to reduce the phytotoxicity, so that the weeds' growth is inhibited, while growth of the desired crops is not.

OBJECT AND SUMMARY OF THE INVENTION

Present invention introduces PGR safener additives for improving growth of Round-Up Ready crops, when Glyphosate solution is applied to such crops, without reducing the growth-inhibiting capacity of Glyphosate.

DETAILED DESCRIPTION OF THE PREFERRED EMBODIMENT

Prepare Glyphosate solution at the concentration as instructed by the manufacturer.

The ways to prepare Glyphosate solution are disclosed in various literatures, such as government agency, universities and manufacturer's instruction, and are generally known to people in the agricultural and herbicide businesses.

For example, the manufacturer of Round-Up Pro (Monsanto Corp) gave its instruction on its product label (dated November, 2002), section 6.0 (Mixing). Specifically, the amount of active Glyphosate ingredient for use in hand-held spraying is stated in a table in section 6.3, covering the desired volume from one gallon to 100 gallons, having concentration from 0.5% to 10%, as shown in Exhibit A, which is a sample Round-Up product label of Monsanto Co., as of the year 2002.

The instruction in Exhibit A is incorporated by reference for its complete content and attached herein.

In an article by Mark Czarnota, Ph.D., of University of Georgia, College of Agricultural and Environmental Sciences, Department of Horticulture, Georgia, titled "Controlling Vines in Ornamentals", Dr. Czarnota mentioned the use of a 5 percent Glyphosate solution and added the mixing instruction as approximately 6 oz of Glyphosate/gallon of water, using a product containing 41 percent active Glyphosate.

The instruction is incorporated by reference for its content and attached herein as Exhibit B.

Although the original producer of Glyphosate stated in its Round-Up label as having concentration from 0.5% to 10%, present invention can be used, by people reasonably skilled in the art, in any concentration applicable as the situation call for. For examples, present invention can be used on the three (3) Glyphosate solutions at the concentration as stated in the data sheets, which were previously provided to Patent Office in inventors' Nov. 7, 2005 communication:

QuickPRO (Glyphosate concentration can be as high as 73%)

Gly Star (Glyphosate concentration can be as high as 41%)

FARMSAVER (Glyphosate concentration can be as high as 41%)

The 3 different kinds of safeners and their mixes are introduced below.

Dilute Cytokinin (Kinetin 0.15%-0.50%) in water at concentration of 1:1000 by volume. This is the Cytokinin Safener.

Dilute 3-Indolebutyric Acid (0.85% IBA) in water at concentration of 1:1000 by volume. This is the IBA Safener.

Dilute 1-Naphthaleneacetic Acid (0.20% NAA) in water at concentration of 1:1000 by volume. This is the NAA Safener.

Dilute Cytokinin (Kinetin) Safener to Glyphosate solution at concentration of 1:1 by volume. This is the Cytokinin Mix.

Dilute Cytokinin (Kinetin) Safener and IBA Safener to Glyphosate solution at concentration of 0.5:0.5:1 by volume. This is the Cytokinin-IBA Mix.

Dilute Cytokinin (Kinetin) Safener, IBA Safener and NAA Safener to Glyphosate solution at concentration of 0.33:0.33:0.34:1 by volume. This is the Combo Mix.

When seedlings of Glyphosate-tolerant crops, such as maize and soybean, are about 4 weeks old, spray the Glyphosate solution to the crops in the manners described by the instructions of Glyphosate solution will cause some crop phototoxicity.

The Glyphosate-tolerant crops will show better growth when Glyphosate is applied to the crops along with the 3 Mixes identified above, than when the Glyphosate-tolerant crops are just sprayed with Glyphosate solution alone.

The invention claimed is:

1. A composition of plant growth regulators (PGRs) for application to Glyphosate-tolerant crops, from the mixture by volume in the ratio of 1:1 of two ingredients, consisting essentially of:
    a. Glyphosate solution; and
    b. Cytokinin Safener obtained by diluting Cytokinin (Kinetin, 0.15%-0.50%) in water at concentration of 1:1000 by volume.

2. A composition of plant growth regulators (PGRs) for application to Glyphosate-tolerant crops, from the mixture by volume in the ratio of 1:0.5:0.5 of three ingredients, consisting essentially of:
   a Glyphosate solution;
   Cytokinin Safener obtained by diluting Cytokinin (Kinetin, 0.15%-0.50%) in water at concentration of 1:1000 by volume; and,
   c. IBA Safener obtained by diluting 3-Indolebutyric Acid (0.85% IBA) in water at concentration of 1:1000 by volume.

3. A composition of plant growth regulators (PGRs) for application to Glyphosate-tolerant crops, from the mixture by volume in the ratio of 1:0.33:0.33:0.34 of four ingredients, consisting essentially of:
   a. Glyphosate solution;
   b. Cytokinin Safener obtained by diluting Cytokinin (Kinetin, 0.15%-0.50%) in water at concentration of 1:1000 by volume;
   c. IBA Safener obtained by diluting 3-Indolebutyric Acid (0.85% IBA) in water at concentration of 1:1000 by volume; and,
   d. NAA Safener obtained by diluting 1-Naphthaleneacetic Acid (0.20% NAA) in water at concentration of 1:1000 by volume.

* * * * *